United States Patent [19]
Tucek

[11] Patent Number: 6,013,096
[45] Date of Patent: Jan. 11, 2000

[54] HAND-HELD LASER LIGHT GENERATOR DEVICE

[76] Inventor: Kevin B. Tucek, 6442 S. Holland Ct., Littleton, Colo. 80123

[21] Appl. No.: 08/971,880

[22] Filed: Nov. 19, 1997

Related U.S. Application Data

[60] Provisional application No. 60/031,620, Nov. 22, 1996.

[51] Int. Cl.[7] .................................. A61N 21/00
[52] U.S. Cl. .................... 607/89; 606/2; 606/13
[58] Field of Search .................... 606/2, 3, 9, 10, 606/13, 17; 607/1, 88–94; 219/219, 220, 227

[56] References Cited

U.S. PATENT DOCUMENTS

| | | | |
|---|---|---|---|
| 4,608,978 | 9/1986 | Rohr | 607/93 |
| 4,733,660 | 3/1988 | Itzkan | 606/17 |
| 4,784,135 | 11/1988 | Blum et al. | 606/3 |
| 4,905,690 | 3/1990 | Ohshiro et al. | 607/89 |
| 5,474,528 | 12/1995 | Meserol | 607/90 |
| 5,755,752 | 5/1998 | Segal | 606/3 |

*Primary Examiner*—Linda C. M. Dvorak
*Assistant Examiner*—Bryan K. Yarnell
*Attorney, Agent, or Firm*—Flanagan & Flanagan; John K. Flanagan; John R. Flanagan

[57] ABSTRACT

A hand-held laser light generator device includes a wand, a semiconductor diode laser for generating a beam of laser light, an optical arrangement, a housing having an interior chamber, a battery in the housing interior chamber, an electrical cord connecting the laser in the wand with the battery in the housing, an electronic timing circuit, a start switch and a selector knob. The wand, capable of being retained in a user's hand, is an elongated hollow tube and defines an interior cavity. The laser is mounted in the wand interior cavity and therewith is freely movable so as to enable the user to direct the beam of laser light onto a desired location. The optical arrangement mounted in the wand interior cavity receives and transforms the generated beam of laser light into a line of laser light. The electrical timing circuit is disposed in the housing interior chamber and mounted to the housing. The start switch is activatable between on and off positions while the selector knob has multiple period of time length setting positions. The start switch and selector knob are mounted to the housing and accessible at the exterior thereof and are in operable communication with the electrical timing circuit for controlling initiation of generation of and length of the period of time that the laser light beam is generated.

19 Claims, 4 Drawing Sheets

HAND-HELD LASER LIGHT GENERATOR DEVICE

This application claims the benefit of U.S. provisional application No. 60/031,620, filed Nov. 22, 1996.

BACKGROUND OF THE INVENTION

1. Field of the Invention

The present invention generally relates to the use of laser lights in medicine and, more particularly, is concerned with a hand-held laser light generator device for use in medical therapy.

2. Description of the Prior Art

Laser lights have a variety of applications. The term "laser" is an acronym for light amplification by estimulated emission of radiation. Thus, a laser is basically a device which generates and amplifies light, and does so in the form of an intense coherent beam. Typically, lasers generate such energy in the ultra-violet, visible, or infrared spectrum.

A laser employing helium-neon gas has been one of the most commonly-used and economical of all lasers. It has found applications ranging from construction alignment to laboratory research because of its ability to produce a beam having a power ranging from a fraction of a milliwatt to a few tens of milliwatts and a wavelength of 632.8 nanometers (nm) falling in the red color spectrum. A helium-neon laser is basically a gas-filled tube, with internal electrodes exciting the gas to emit light. Mirrors at each end of the tube define the laser cavity. One mirror is totally reflective, while the other one at the opposite end of the cavity transmits the fraction of the light that becomes the external laser beam.

One of the many diverse applications for helium-neon lasers is medical. Helium-neon lasers are used in several types of medical therapy, primarily so-called unconventional treatments such as laser acupuncture, bio-stimulation, stimulation of wound healing, and alleviation of pain. Helium-neon lasers are used by the more orthodox medical establishment in instruments which count cells by measuring light scattering and which measure other quantities of medical interest. They also have other medical-related uses, such as helping align persons in x-ray imaging systems.

Helium-neon lasers as well as other types of lasers that have been used heretofore in the aforementioned unconventional medical applications are large in size, have complicated controls and thus are difficult to maneuver and operate. These drawbacks have prevented these lasers from reaching their full potential in such medical applications and thus have impeded the widespread use and acceptance of lasers.

Consequently, a need still exists for a device which provides a solution to the aforementioned problems in the prior art without introducing any new problems in place thereof.

SUMMARY OF THE INVENTION

The present invention provides a hand-held laser light generator device which is designed to satisfy the aforementioned need. The hand-held laser light generator device of the present invention is intended to be used in medical therapy. The hand-held laser light generator device is compact in size and has simple controls which are easy to use. The hand-held laser light generator device includes a laser which is freely movable so as to enable the user to direct a beam of light onto a desired location, such as on a surface of skin of a patient being contacted by the beam of light.

Accordingly, the present invention is directed to a hand-held laser light generator device which comprises: (a) a wand defining an interior cavity and capable of being retained in a hand of a user; (b) means for generating a beam of laser light mounted in the interior cavity of the wand and therewith being freely movable so as to enable the user to direct the beam of laser light onto a desired location; (c) an optical arrangement mounted in the interior cavity of the wand for receiving the generated beam of laser light from the generating means and transforming the generated beam of laser light into a line of laser light; (d) a housing defining an interior chamber and having an exterior; (e) means for supplying electrical power to the generating means being disposed in the interior chamber of the housing; (f) means for electrically interconnecting the laser light beam generating means and the electrical power supplying means; and (g) means for controlling a period of time the beam of laser light is generated. The beam of laser light that is generated delivers energy to a human body in a form which is believed to assist in cell regeneration and to increase the size of capillaries to improve blood flow and circulation.

More particularly, the wand is a substantially elongated hollow tube having an open forward end and a rear end. The generating means is a semiconductor diode laser preferably using less than one watt of power. The generated beam of laser light is in the visible/UV energy spectrum and has a wavelength of about 635 nm and a red color. The optical arrangement in the wand includes a collimating lens and a line generating prism. The collimating lens and line generating prism are disposed in a serial relation to the laser between the open forward end of the wand and the laser. The collimating lens and line generating prism transform the generated beam of laser light into the line of laser light.

The housing also has a cradle preferably mounted to a side of the exterior of the housing for releasably securing the wand thereto and a clip mounted preferably to the rear of the exterior of the housing for releasably securing the housing to an article of clothing worn by the user. The electrical power supplying means is preferably a battery which supplies power the laser. The electrical interconnecting means is an electrical cord having opposite ends, one of the opposite ends being attached to the wand and making electrical connection with the laser, the other of the opposite ends being attached to the housing and making electrical connection with the battery.

The time period controlling means includes an electrical timing circuit disposed in the interior chamber of and mounted to the housing, a start switch activatable between on and off positions, and a selector knob having multiple time period length setting positions. The start switch and selector knob are mounted to the housing and are accessible at the exterior thereof. The start switch and selector knob are in operable communication with the electrical timing circuit for controlling the initiation of generation of the beam of laser light and the length of the period of time the beam of laser light is generated. The time period controlling means may further include a lock mechanism mounted to the housing and a key for actuating the lock mechanism between a first position in which the lock mechanism permits the start switch to be activated to the on position and a second position in which the lock mechanism prevents the start switch from being activated to the on position.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

DETAILED DESCRIPTION OF THE INVENTION

Figures 1, 2, 3:
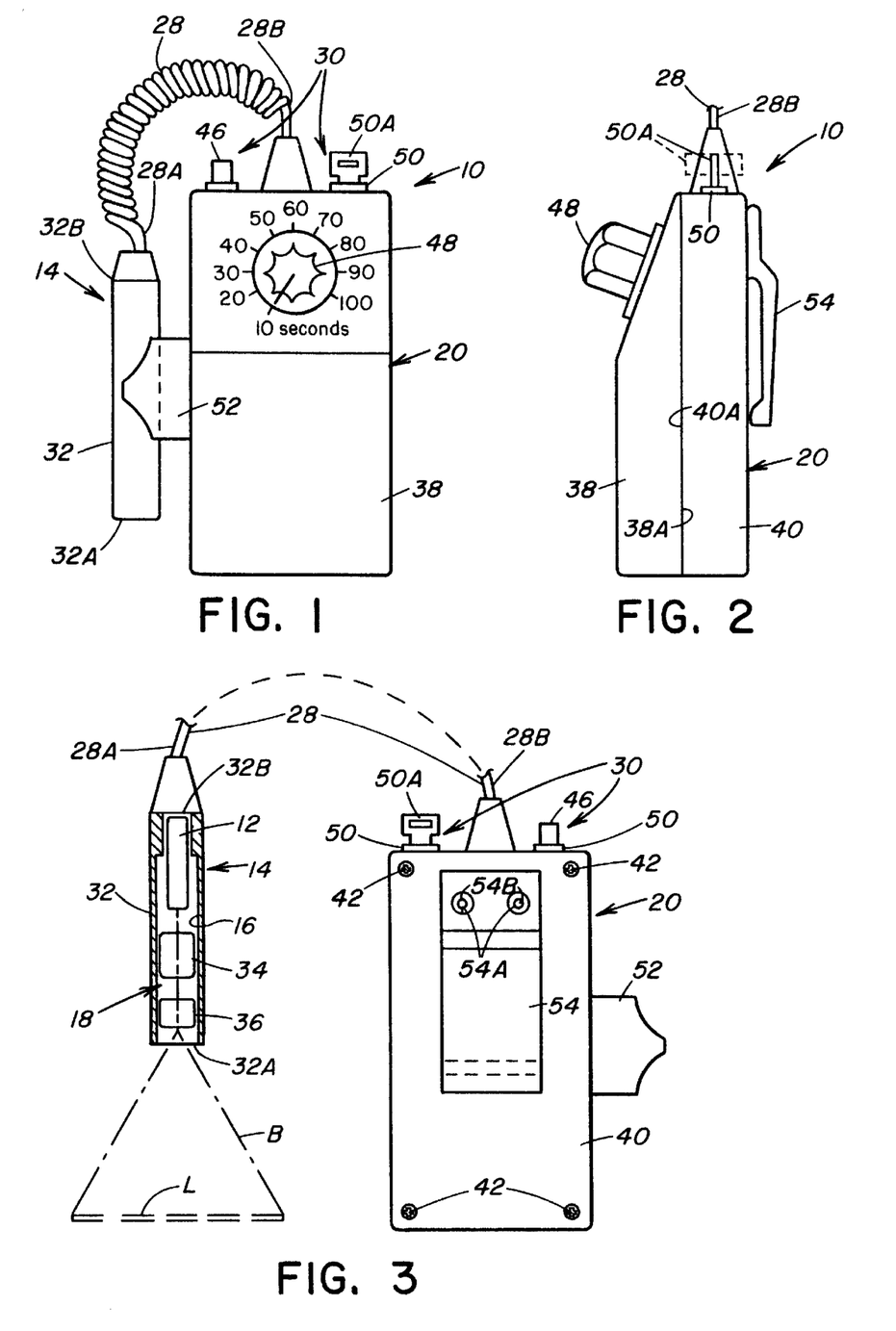
FIG. 1 is a front elevational view of a hand-held laser light generator device of the present invention.
FIG. 2 is a side elevational view of the device.
FIG. 3 is a partially fragmented and partially sectioned rear elevational view of the device.
Figure 4:
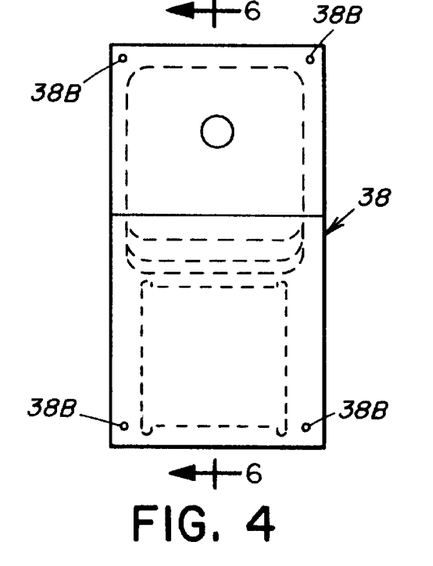
FIG. 4 is a front elevational view of a front cover of a housing of the device.
Figure 5:
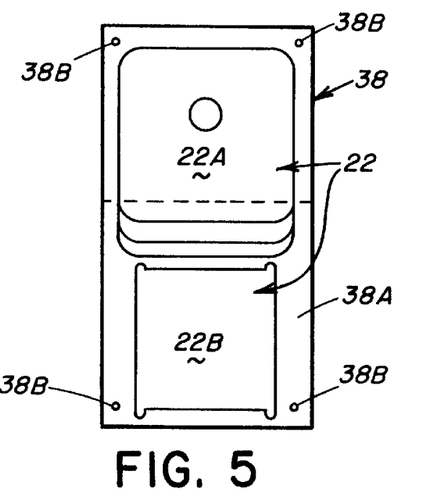
FIG. 5 is a rear elevational view of the front cover of the housing.
Figure 6:
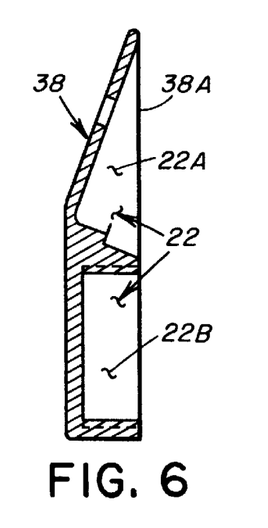
FIG. 6 is a longitudinal sectional view of the front cover as seen along line 6—6 of FIG. 4.
Figure 7:
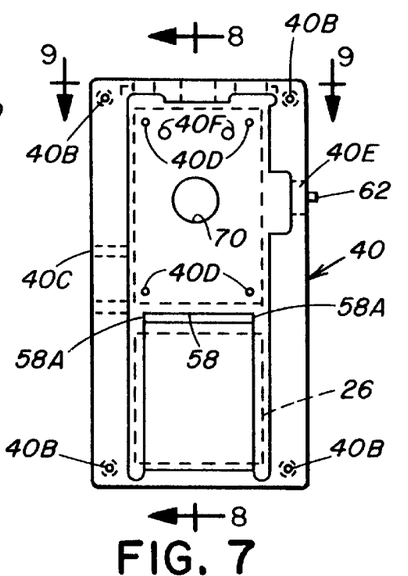
FIG. 7 is a rear elevational view of a back base of the housing.
Figure 8:
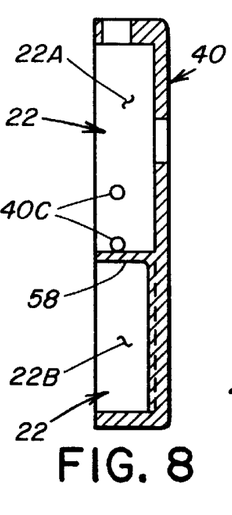
FIG. 8 is a longitudinal sectional view of the back base as seen along line 8—8 of FIG. 7.
Figure 9:
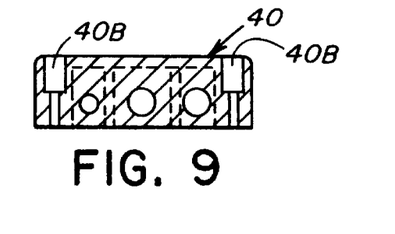
FIG. 9 is a transverse sectional view of the back base as seen along line 9—9 of FIG. 7.
Figures 10, 11, 12, 13, 14, 15, 16:
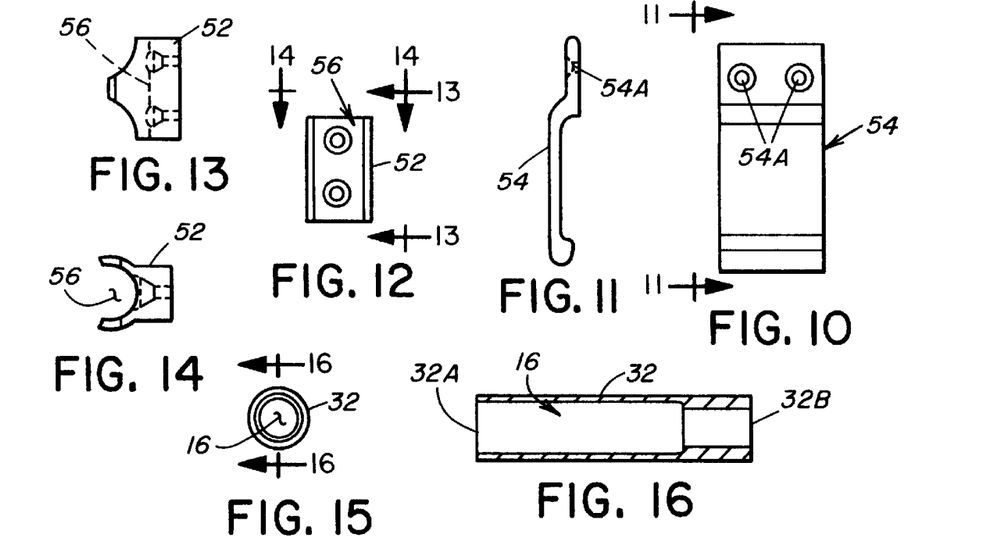
FIG. 10 is a front elevational view of a clip on the housing.
FIG. 11 is a side elevational view of the clip as seen along line 11—11 of FIG. 10.
FIG. 12 is a front elevational view of a cradle on the housing.
FIG. 13 is a side elevational view of the cradle as seen along line 13—13 of FIG. 12.
FIG. 14 is a top plan view of the cradle as seen along line 14—14 of FIG. 12.
FIG. 15 is a forward end elevational view of a wand of the device.
FIG. 16 is a longitudinal sectional view of the wand as seen along line 16—16 of FIG. 15.

Referring to the drawings and particularly to FIGS. 1 to 3, there is illustrated a hand-held laser light generator device, generally designated 10, of the present invention, for use in applications, such as medical therapy. The hand-held laser light generator device 10 emits a beam of laser light B, preferably, with an 80° to 85° spread in a relatively narrow planar configuration to substantially form a line of light L on a surface of skin of a patient being contacted by the laser light beam B. The laser light beam B delivers energy to the human body in a form which is believed to assist in cell regeneration and to increase the size of capillaries to improve blood flow and circulation.

The hand-held laser light generator device 10 basically includes laser module 12 for generating the laser light beam B and a wand 14 defining an interior cavity 16 and capable of being retained in a hand of a user. The laser module 12 is mounted in the interior cavity 16 of the wand 14. The laser module 12 with the wand 14 is thereby freely movable in the user's hand so as to enable the user to direct the laser light beam B onto a desired location. The hand-held laser light generator device 10 also includes an optical arrangement 18 mounted in the interior cavity 16 of the wand 14 for receiving the generated beam of laser light beam and transforming it into the line of laser light L, as represented in FIG. 3.

The hand-held laser light generator device 10 further includes a housing 20 defining an interior chamber 22 and having an exterior 24, an electrical power supplying means 26 in the form of a battery for supplying electical power to the laser module 12 being disposed in the interior chamber 22 of the housing 20, an electrical cord 28 having opposite ends 28A, 28B interconnecting the wand 14 with the housing 20, and controlling means 30 for controlling the period of time the beam of laser light B is generated. Specifically, the one end 28A of the cord 28 attached to the wand 14 makes electrical connection with the laser module 12 while the other end 28B of the cord 28 attached to the housing 22 makes electrical contact with the controlling means 30 and battery 22. The electrical cord 28 is spirally-wound and provides insulation for one or more electrical conductor wires disposed therein.

The wand 14 of the device 10 is a substantially elongated hollow tube 32, but can have any other suitable configuration. The tube 32 of the wand 14 has a forward end 32A and a rear end 32B. The wand 14 is open at the forward end 32A and tapers to an opening defined by the rear end 32B. The laser module 12 of the device 10 preferably is a semiconductor diode laser, which is of a well-known and standard construction. The laser module 12 uses less than one watt of power, though may use any other suitable amount of power. The generated laser light beam B preferably is in the visible/UV energy spectrum, has a wavelength of about 635 nm and a red color, but may be any other suitable type for a particular application.

The optical arrangement 18 of the device 10 includes a collimating lens 34 and a line generating prism 36. The collimating lens 34 and the line generating prism 36 are disposed in serial relation to the laser module 12. The optical arrangement 18 is particularly disposed between the open forward end 32A of the wand tube 32 and the laser module 12. The collimating lens 34 and the line generating prism 36 receive and transform the generated beam of laser light B into the line of laser light L. As an alternative, a suitable mechanical arrangement could be substituted for the optical arrangement 18. As can be clearly understood from FIG. 3, the planar beam of laser light B is disposed externally of the wand 14 and produces a line of laser light L preferably in the red color spectrum at a desired location on the suface of the patient's skin and with the line of laser light L being visible to the user as the X and 14 is held and freely moved by the user in a spaced relationship from and out of contact with the patient.

Referring now to FIGS. 1–9, the housing 20 of the device 10 has a front cover 38 and a back base 40. The front cover 38 has a rear planar surface 38A and defines alignable corner holes 38B. The back base 40 has a front planar surface 40A and defines alignable corner holes 40B. The rear planar surface 38A of the front cover 38 and the front planar surface 40A of the back base 40 fit flush together and are secured together by the alignable corner holes 38B, 40B which are adapted to threadably receive fastening screws 42. The front cover 38 and back base 40 give the housing 20 a substantially rectangular shape, but for an upper front surface 38C defined by the front cover 38 which is substantially inclined, though may have any other suitable shape. The front cover 38 and the back base 40 together define respective portions of the interior chamber 22 of the housing 20.

Figure 19:
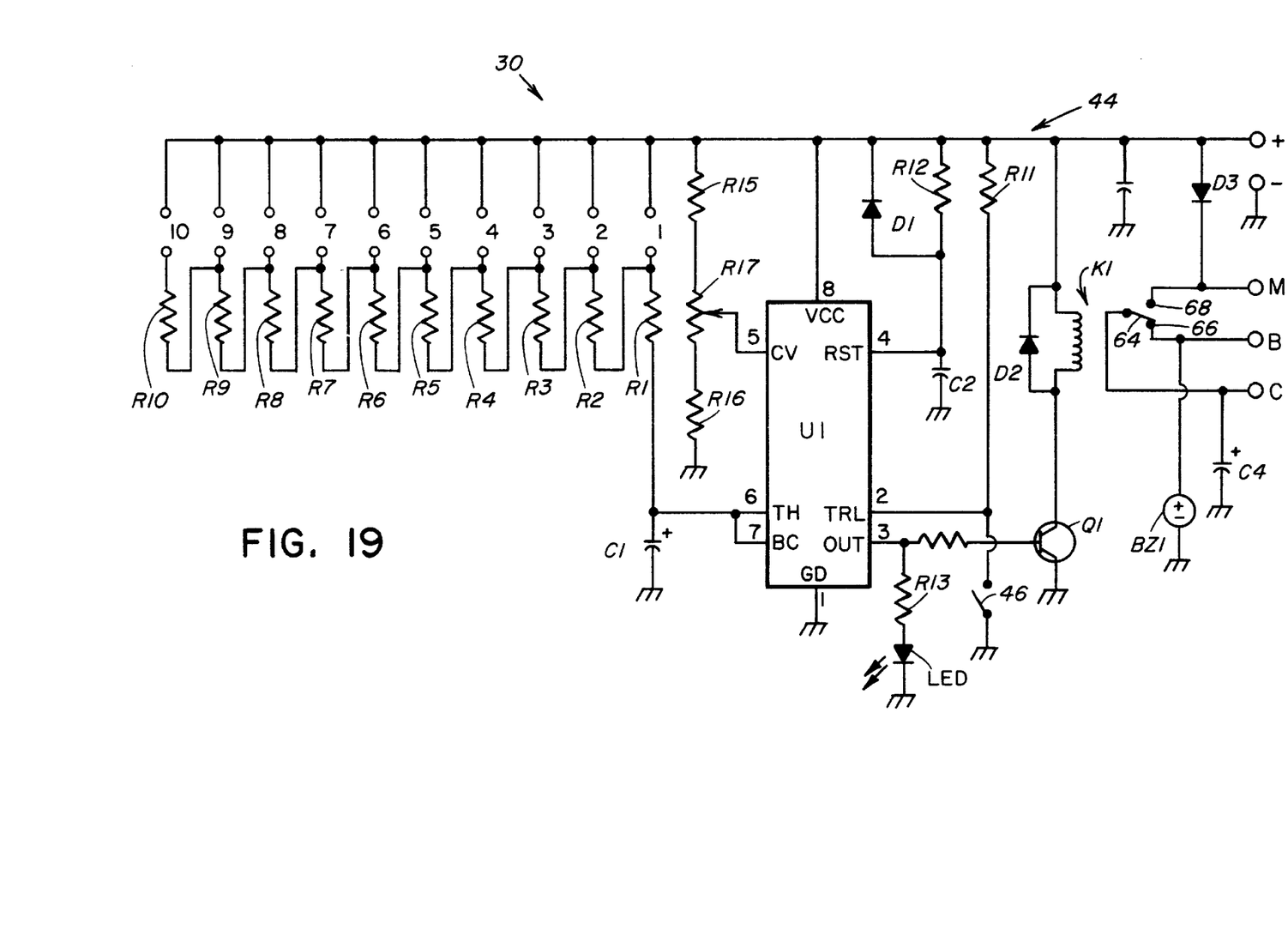
FIG. 19 is an electrical schematic view of the electrical timing circuit of FIG. 17.

Referring now to FIGS. 1–19, the controlling means 30 of the device 10 includes an electrical timing circuit 44 disposed in the interior chamber 22 of the housing 20 and being mounted to the housing 20, a start switch 46, preferably of the push button type, activatable between on and off positions (as seen in FIG. 19), and a selector knob 48, preferably of the rotary type, having multiple period of time length setting positions, as shown in FIGS. 1 and 19. The start switch 46 and selector knob 48 are mounted to the housing 20 and are accessible at the exterior 24 thereof and are in operable communication with the electrical timing circuit 44 for controlling the initiation of generation of beam of laser light B and the length of the period of time that the beam of laser light B is generated, such as from ten to one hundred seconds. More particularly, the push button start switch 46 is mounted to the top 40 of the back base 40 and the rotary selector knob 48 is mounted to the upper front surface 38 of the front cover 38.

The controlling means 30 of the device 10 may further include a lock mechanism 50 mounted to the housing 20 and a key 50A insertable in the lock mechanism 50 for actuating the lock mechanism 50 between first and second positions. In the first position of the key 50A shown in solid line form in FIG. 2, the lock mechanism 50 permits the start switch 46 to be activated to the on (or closed) position whereas in the second position of the key 50A shown in dashed line form in FIG. 2, the lock mechanism 50 prevents the start switch 46 from being activated to the on position.

The housing 20 of the device 10 further has a cradle 52 mounted to the exterior 24 of the housing 20 for releasably securing the wand 14 thereto, and a clip 54 mounted to the exterior 24 of the housing 20 for releasably securing the housing 20 of the device 10 to an article of clothing, such as a belt, worn by the user. The cradle 52, as seen particularly in FIGS. 1, 3 and 12–14, is on one side of the back base 40. This one side of the back base 40 defines a pair of apertures 40 and the cradle 52 defines a pair of apertures 52A being alignable therewith for receiving suitable fasteners (not shown) to fixedly attach the cradle 52 to the one side of the back base 40. The cradle 52 defines a circular slot 56 having a diameter chosen relative to the diameter of the wand 14 so that the wand 14 can be slidably placed through the slot 56 in a relatively tight-fitting relationship and thereby retained by the cradle 52 in a storage position alongside the housing 20. The wand 14 is only withdrawn from the cradle 52 when it is desired to operate the device 10.

The clip 54, as seen particularly in FIGS. 2, 3, 10 and 11, is on a back wall 40 of the back base 40. This back wall 40 of the back base 40 defines a pair of holes 40. The clip 54 defines a pair of apertures 54A alignable therewith for receiving suitable fasteners 54B to fixedly attach the clip 54 to the back wall 40 of the back base 40.

The back base 40 further has a horizontal shelf or partition 58 which extends between the back base 40 and front cover 38 so as to divide the interior chamber 22 into upper and lower interior chambers 22A, 22B. The electrical timing circuit 44 includes a circuitboard 60 containing the components thereof and is supported vertically upon the partition 58 in the upper chamber 22A. The circuitboard 60 has corner openings 60A alignable with corresponding openings 40 defined by the back wall 40 of the back base 40 to receive suitable fasteners (not shown) for securing the circuitboard 60 in the upper chamber 22A in the position shown in dashed outline in FIG. 7. The battery 26, which can be any commercially-available and rechargeable d.c. battery, is represented by the dashed outline 26 in FIG. 7 and is housed in the lower chamber 22B. Opposite ends 58A of the partition 58 are spaced inwardly from opposite sides of the back base 40 allowing clearance for passage of electrical conductor wires (not shown) to the rechargeable battery 26 from a recharger electrical plug 62 mounted through an opening 40 defined in the other side of the back base 40 opposite from the location of the cradle 52.

Figure 17:
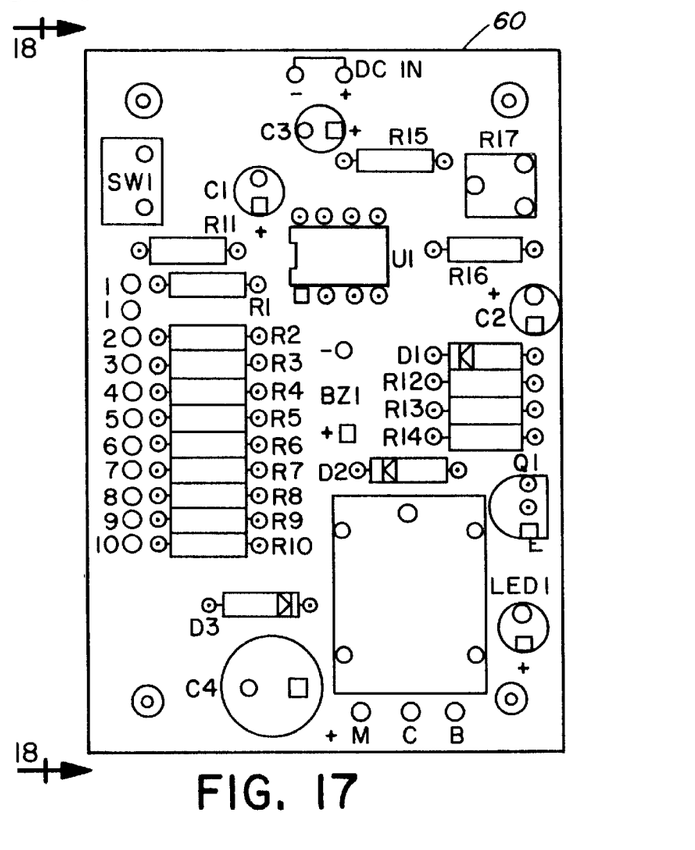
FIG. 17 is an enlarged plan view of a circuitboard containing an electrical timing circuit of a time period controlling means of the device.
Figure 18:
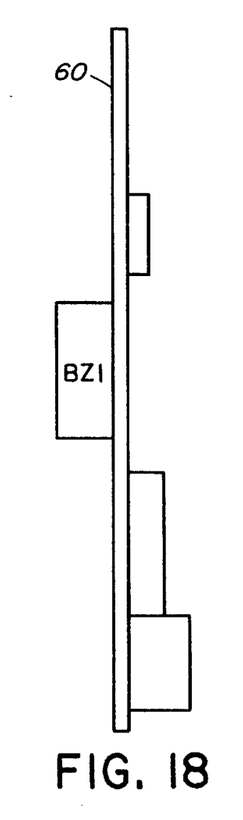
FIG. 18 is a side elevational view of the circuitboard as seen along line 18—18 of FIG. 17.

Referring now to FIGS. 17–19, the electrical timing circuit 44 includes components having the designations and values listed in Table I. These components are mounted on the circuitboard 60.

TABLE I

| Components | Designations | Values |
|---|---|---|
| Resistors | R1–R10, R12 | 1M ohms |
| Resistors | R11, R13 | 100K ohms |
| Resistors | R15–R16 | 10K ohms |
| Potentiometer | R17 | variable |
| Resistor | R14 | 6.5K ohms |
| Diodes | D1–D3 | MA150 |
| Capacitor | C1 | 10 uF |
| Capacitor | C2 | 1 uF |
| Capacitor | C3 | 100 uF |
| Capacitor | C4 | 1000 uF |
| Push Button Switch | 46 | n/a |
| Timer | U1 | Type 555 |
| L.E.D. | LED1 | n/a |
| Buzzer | BZ1 | n/a |
| Relay | K1 | n/a |
| Transistor Amp. | Q1 | 2N 3706 ECB |

The hand-held laser light generator device 10 can operate as follows. The timer U1 is provided in a monostable multivibrator mode of operation in which the duration of a timing output signal produced by the timer U1 is determined by the ones of resistors R1–R10 which are connected to the capacitor C1 and the threshold and discharge pins 6 and 7 of the timer U1. The rotational position of the rotary selector knob 48 determines which of the resistors R1–R10 are so connected. Resistors R1–R10 are connected in series with one another and through pairs of contacts going from #1 to #10 successively more of the resistors can be connected with the positive (+) terminal of the battery 26. The resistor R1 being the closest to the timer U1 and capacitor C1 is the first one so connected when the rotary selector knob 48 is located at the ten (10) second setting as seen in FIG. 1. As the selector knob 48 is rotated clockwise the timing period can be lengthened from the lowest setting of ten (10) seconds to the longest setting of one hundred (100) seconds. At each successive one of the ten settings, the knob 48 closes a different one of successive pairs of contacts #1–#10. Each successive pair that is closed increases by one the number of resistors brought into series with the positive (+) terminal of the battery 26 and the timer U1. Thus, more resistance is added with each successive increasing setting of selector knob 48.

With the key 52 in its first position, pushing the button of the start switch 46 closes the circuit and allows a flow of current to the trigger input pin 2 of the timer T1 causing generation of a timing signal or pulse from the output pin 3 of the timer T1 for a period of time equal to the setting of the selector knob 48. The output timing signal from the timer T1 is amplified by transistor Q1 and actuates the relay K1 so that its contact arm 64 switches positions from engagement with the first contact 66 to engagement with the second contact 68. The output timing signal via the actuated or latched relay K1 also energized the circuit through the laser module 12 connected between the (−) terminal of the battery 26 and the terminal C of the circuitboard 60 and turns "on" the laser module 12. The contact arm 64 is latched or held at the new position for the duration of the output timing signal from timer T1. During this period, the capacitor C4 is charged up so that at the end of the timing signal when the relay K1 is unlatched and its contact arm 64 returns to engagement with the first contact 66, the capacitor C4 will then discharge through the buzzer BZ to ground and cause the buzzer BZ to generate a beeping sound which informs the user that the laser module 12 has shut off. Also during the period of the output timing signal the LED is turned on indicating that the beam of laser light B is being generated. The LED is mounted within the push button start switch 46 which is transparent.

Thus, at the start of the timed cycle, the timer T1 turns on the LED light and the laser module 12 to cause the latter to generate the beam of laser light B. The capacitor C4 is charged during the timed cycle. At the end of the timed cycle, the timer T1 turns off the LED light and the laser module 12. The capacitor C4 is discharged through the buzzer BZ causing a beeping to inform the user that the time has expired. The buzzer BZ is disposed adjacent to an opening 70 defined through the back base 40 in spaced relationship to and behind the clip 54. The opening 70 permits the beeping to be readily heard outside of the housing 20 by the user. The key 52 can be removed from the lock mechanism 50 so that the device 10 cannot be used nor accidentally turned on. To recharge, the recharger plug 62 is connected to a 110 vac wall socket for about six to eight hours.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. A hand-held laser light generator device for use in medical therapy, said device comprising:
    (a) a wand in the form of a substantially elongated hollow tube defining an interior cavity and capable of being retained in a hand of a user and freely moved relative to the surface of the skin of a patient to receive the medical therapy;
    (b) means mounted in said interior cavity of said wand for generating a beam of laser light in the red color spectrum;
    (c) an optical arrangement mounted in said interior cavity of said wand for receiving the red color spectrum generated beam of laser light from said generating means and for transforming the generated beam of laser light into a substantially planar beam of laser light disposed externally of said wand for producing a line of laser light in the red color spectrum at a desired location on the surface of the patient's skin and with said line of laser light being visible to the user as said wand is held and freely moved by the user in a spaced relationship from and out of contact with the patient;
    (d) a housing defining an interior chamber and having an exterior;
    (e) means disposed in said interior chamber of said housing for supplying electrical power to said laser beam generating means;
    (f) means for electrically interconnecting said laser beam generating means and said electrical power supplying means such that said wand is movable relative to said housing; and
    (g) means on said housing for controlling a period of time said beam of laser light is generated.

2. The device of claim 1 wherein said generating means is a semiconductor diode laser using less than one watt of power.

3. The device of claim 1 wherein the generated said beam of light has a wavelength of about 635 nm.

4. The device of claim 1 wherein said optical arrangement includes:
    a collimating lens; and
    a line generating prism, said collimating lens and line generating prism being disposed in a serial relation to said generating means.

5. The device of claim 1 wherein said electrical power supplying means is a battery.

6. The device of claim 1 wherein said controlling means includes:
    an electrical timing circuit disposed in said interior chamber of and being mounted to said housing;
    a start switch activatable between on and off positions; and
    a selector knob having multiple period of time length setting positions, said start switch and selector knob being mounted to said housing and accessible at said exterior thereof and being in operable communication with said electrical timing circuit for controlling initiation of generation of said beam of laser light and length of the period of time said beam of laser light is generated.

7. The device of claim 6 wherein said controlling means further includes:
    a lock mechanism mounted to said housing; and
    a key for actuating said lock mechanism between a first position in which said lock mechanism permits said start switch to be activated to said on position and a second position in which said lock mechanism prevents said start switch from being activated to said on position.

8. The device of claim 1 wherein said housing further has a cradle mounted to and projecting outwardly from said exterior of said housing for releasably securing said wand thereto, said cradle defining an annular slot open at opposite ends such that said tubular wand can be removably and slidably placed through said slot in a relatively tight-fitting relationship with said cradle and thereby retained by said cradle in a storage position spaced from and alongside said housing.

9. The device of claim 1 wherein said housing further has a clip mounted to said exterior of said housing for releasably securing said housing to an article of clothing worn by the user.

10. A hand-held laser light generator device for use in medical therapy, said device comprising:
    (a) a wand in the form of a substantially elongated hollow tube defining an interior cavity and capable of being retained in a hand of a user and freely moved relative to the surface of the skin of a patient to receive the medical therapy;
    (b) a semiconductor diode laser mounted in said interior cavity of said wand for generating a beam of laser light in the red color spectrum;
    (c) an optical arrangement mounted in said interior cavity of said wand for receiving the red color spectrum generated beam of laser light from said generating means and for transforming the generated beam of laser light into a substantially planar beam of laser light disposed externally of said wand for producing a line of laser light in the red color spectrum at a desired location on the surface of the patient's skin and with said line of laser light being visible to the user as said wand is held and freely moved by the user in a spaced relationship from and out of contact with the patient;

(d) a housing defining an interior chamber and having an exterior;

(e) a battery disposed in said interior chamber of said housing for supplying electrical power to said laser;

(f) an electrical cord having opposite ends, one of said opposite ends being attached to said wand and making electrical connection with said laser, the other of said opposite ends being attached to said housing and making electrical connection with said battery such that said wand is movably relative to said housing; and (g) means for controlling a period of time said beam of laser light is generated, said controlling means including
  (i) an electrical timing circuit disposed in said interior chamber of and being mounted to said housing,
  (ii) a start switch activatable between on and off positions,
  (iii) a selector knob having multiple period of time length setting positions, said start switch and selector knob being mounted to said housing and accessible at said exterior thereof and being in operable communication with said electrical timing circuit for controlling initiation of generation of said beam of laser light and length of the period of time said beam of laser light is generated,
  (iv) means electrically activatable for generating a sound audible to the user, and
  (v) means electrically connected to said timing circuit and said sound generating means for electrically charging in response to said beam of laser light being generated and for electrically discharging and thereby electrically activating said sound generating means in response to termination of generation of said beam of laser light.

11. The device of claim 10 wherein said laser uses less than one watt of power.

12. The device of claim 10 wherein said generated said beam of laser light has a wavelength of about 635 nm.

13. The device of claim 10 wherein said optical arrangement includes;
  a collimating lens; and
  a line generating prism, said collimating lens and line generating prism being disposed in a serial relation to said laser.

14. The device of claim 10 wherein said controlling means further includes:
  a lock mechanism mounted to said housing; and
  a key for actuating said lock mechanism between a first position in which said lock mechanism permits said start switch to be activated to said on position and a second position in which said lock mechanism prevents said start switch from being activated to said on position.

15. The device of claim 10 wherein said housing further has a cradle mounted to and projecting outwardly from said exterior of said housing for releasably securing said wand thereto, said cradle defining an annular slot open at opposite ends such that said tubular wand can be removably and slidably placed through said slot in a relatively tight-fitting relationship with said cradle and thereby retained by said cradle in a storage position spaced from and alongside said housing.

16. The device of claim 10 wherein said housing further has a clip mounted to said exterior of said housing for releasably securing said housing to an article of clothing worn by the user.

17. A hand-held laser light generator device for use in medical therapy, said device comprising:

(a) a wand in the form of a substantially elongated hollow tube defining an interior cavity and capable of being retained in a hand of a user and freely moved relative to the surface of the skin of a patient to receive the medical therapy;

(b) a semiconductor diode laser mounted in the interior cavity of said wand and using less than one watt of power for generating a beam of laser light in the red color spectrum and having a wavelength of about 635 nm;

(c) an optical arrangement mounted in said interior cavity of said wand and including
  (i) a collimating lens, and
  (ii) a line generating prism, said collimating lens and line generating prism being disposed in a serial relation to said laser such that said beam of laser light in said red color spectrum generated by said laser is received and transformed into a substantially planar beam of laser line disposed externally of said wand for producing a line of laser light in the red color spectrum at a desired location on the surface of the patient's skin and with said line of laser light being visible to the user as said wand is held and freely moved by the user in a spaced relationship from and out of contact with the patient;

(d) a housing defining an interior chamber and having an exterior;

(e) a battery disposed in said interior chamber of said housing for supplying electrical power to said laser;

(f) an electrical cord having opposite ends, one of said opposite ends being attached to said wand and making electrical connection with said laser, the other of said opposite ends being attached to said housing and making electrical connection with said battery such that said wand is movable relative to said housing; and (g) means on said housing for controlling a period of time said beam of laser light is generated, said controlling means including
  (i) an electrical timing circuit disposed in said interior chamber of and being mounted to said housing,
  (ii) a push button start switch activatable between on and off positions,
  (iii) a rotary selector knob having multiple period of time length setting positions, said push button start switch and rotary selector knob being mounted to said housing and accessible at said exterior of said housing and being in operable communication with said electrical timing circuit for controlling initiation of generation of and length of the period of time said beam of laser light is generated,
  (iv) a lock mechanism mounted to said housing,
  (v) a key for actuating said lock mechanism between a first position in which said lock mechanism permits said push button start switch to be activated to said on position and a second position in which said lock mechanism prevents said push button start switch from being activated to said on position,
  (vi) means electrically activatable for generating a sound audible to the user, and
  (vii) means electrically connected to said timing circuit and said sound generating means for electrically charging in response to said beam of laser light being generated and for electrically discharging and thereby electrically activating said sound generating means in response to termination of generation of said beam of laser light.

18. The device of claim 17 wherein said housing further has a cradle mounted to and projecting outwardly from said exterior of said housing for releasably securing said wand thereto, said cradle defining an annular slot open at opposite ends such that said tubular wand can be removably and slidably placed through said slot in a relatively tight-fitting relationship with said cradle and thereby retained by said cradle in a storage position spaced from and alongside said housing.

19. The device of claim 17 wherein said housing further has a clip mounted to said exterior of said housing for releasably securing said housing to an article of clothing worn by the user.

* * * * *